(12) United States Patent
Nasralla

(10) Patent No.: US 8,808,541 B2
(45) Date of Patent: Aug. 19, 2014

(54) DIALYSIS CELL AND TRAY FOR DIALYSIS CELLS

(76) Inventor: Marwan Nasralla, Santa Ana, CA (US)

(*) Notice: Subject to any disclaimer, the term of this patent is extended or adjusted under 35 U.S.C. 154(b) by 467 days.

(21) Appl. No.: 12/074,479

(22) Filed: Mar. 3, 2008

(65) Prior Publication Data
US 2009/0218283 A1 Sep. 3, 2009

(51) Int. Cl.
*B01D 61/26* (2006.01)
*B01D 63/00* (2006.01)
*B01D 35/30* (2006.01)
*G01N 1/40* (2006.01)
*B01D 61/28* (2006.01)
*B01L 3/00* (2006.01)

(52) U.S. Cl.
CPC ...... *G01N 1/4005* (2013.01); *G01N 2001/4016* (2013.01); *B01L 3/502* (2013.01); *B01D 61/28* (2013.01); *Y10S 436/809* (2013.01)
USPC ........... 210/321.72; 210/645; 210/321.6; 210/321.71; 210/321.84; 210/500.1; 210/500.27; 435/288.3; 435/288.4; 435/305.1; 435/305.4; 435/297.5; 436/809

(58) Field of Classification Search
CPC ...... B01D 61/28; B01L 3/502; G01N 1/4005; G01N 2001/4016
USPC ......... 210/645, 321.6, 321.72, 321.84, 500.1, 210/500.27; 422/99, 101, 102; 435/288.3, 435/288.4, 305.1, 305.4, 297.5; 436/809
See application file for complete search history.

(56) References Cited

U.S. PATENT DOCUMENTS

| 3,074,559 A | 1/1963 | Savino .......................... 210/321 |
| 3,212,498 A | 10/1965 | McKirdy et al. |
| 3,256,174 A | 6/1966 | Kwo-Wei Chen et al. |
| 3,796,313 A | 3/1974 | Bigt et al. ...................... 210/321 |
| 3,839,204 A | 10/1974 | Ingenito et al. ............... 210/181 |
| 3,907,687 A | 9/1975 | Hoeltzenbein ................ 210/321 |
| 4,071,444 A | 1/1978 | Ash et al. .................... 210/22 A |
| 4,748,124 A | 5/1988 | Vogler ................... 435/240.241 |
| 4,750,983 A | 6/1988 | Foster et al. ................... 204/301 |
| 4,963,256 A | 10/1990 | Nelson .......................... 210/232 |
| 5,106,464 A | 4/1992 | Clifford et al. ................. 204/83 |
| 5,190,878 A | 3/1993 | Wilhelm ....................... 435/285 |
| 5,217,612 A | 6/1993 | Ondrick .................... 210/321.75 |
| 5,266,209 A | 11/1993 | Knight et al. ................. 210/691 |
| 5,445,737 A | 8/1995 | Ondrick .................... 210/321.71 |
| 5,605,835 A | 2/1997 | Hu et al. ..................... 435/297.2 |

(Continued)

OTHER PUBLICATIONS

Booklet of Photos of Dialysis Cassette Sold May 1995.

*Primary Examiner* — Dirk Bass
(74) *Attorney, Agent, or Firm* — David G. Duckworth; Russo & Duckworth, LLP

(57) ABSTRACT

A dialysis cell is provided for the measurement of free thyroxine. The dialysis cell preferably includes a polyhedral housing including a top, a bottom and four sides. The dialysis cell is made up of a buffer portion and serum portion. The buffer portion includes a cavity and the serum portion includes a cavity which, when the buffer portion and serum portion are assembled together, form a central chamber. The central chamber is divided by a vertically aligned dialysis membrane held in place by two O-rings. Buffer is introduced into the dialysis cell's buffer portion through a buffer inlet extending from the dialysis cell's top side to the buffer portion's cavity. Similarly, serum is introduced into the serum portion through an inlet which extends from an opening formed on the dialysis cell's top to the serum portion's cavity.

5 Claims, 3 Drawing Sheets

(56) References Cited

U.S. PATENT DOCUMENTS

| | | | |
|---|---|---|---|
| 5,763,266 A | 6/1998 | Palsson et al. | 435/289.1 |
| 5,888,807 A | 3/1999 | Palsson et al. | 435/293.2 |
| 6,127,141 A | 10/2000 | Kopf | 435/41 |
| 6,329,195 B1 | 12/2001 | Pfaller | 435/297.2 |
| 6,399,363 B1 | 6/2002 | Hammerstedt et al. | 435/286.5 |
| 6,670,173 B1 | 12/2003 | Schels et al. | 435/297.2 |
| 7,056,440 B2 | 6/2006 | Haney et al. | 210/644 |
| 2003/0213740 A1* | 11/2003 | Creasey | 210/321.6 |
| 2006/0102547 A1* | 5/2006 | Huang | 210/321.6 |
| 2007/0215538 A1* | 9/2007 | Periana et al. | 210/321.6 |
| 2007/0280860 A1* | 12/2007 | Goodwin | 422/101 |

* cited by examiner

US 8,808,541 B2

DIALYSIS CELL AND TRAY FOR DIALYSIS CELLS

BACKGROUND OF THE INVENTION

The present invention relates to dialysis cells. Further, the invention relates to a disposable dialysis cell that is economical to manufacture and easy to use. The dialysis cell of the present invention relates to devices for the dialysis of small, fixed-volume samples commonly dialysized in research laboratories. To this end, the device relates to cells which facilitate loading and unloading of samples in a laboratory setting where many specimens are concurrently analyzed.

The early method for the measurement of free thyroxine in serum involved dialysis to separate the free form of the thyroxine from the protein bound form. The partitioning of thyroxine between the free thyroxine and bound thyroxine was estimated by the addition of radio-iodine labeled thyroxine to the serum sample prior to dialysis. The dialysis was carried out by using a diluted serum sample and/or a great excess of dialysate volume to assist in controlling pH.

An improved method for measurement of free thyroxine was described in U.S. Pat. No. 4,963,256 issued to Jerald Nelson. This reference describes a dialysis cell which allows for a direct measurement of free thyroxine by radioimmunoassay which avoids the addition of radio-iodine labeled thyroxine tracers. The dialysis cell is constructed to allow for dialysis of a small volume of buffer against a large volume of a serum sample. At the completion of dialysis, the sample is withdrawn utilizing a pipet for introduction into an RIA tube.

The Nelson dialysis cell has three major parts including a dialysate vial, a membrane cylinder and a cap. The dialysis membrane separates the retentate compartment above a dialysate compartment. Dialysate buffer is introduced into the dialysis chamber, and a serum specimen is introduced into an inner cylinder which is concentrically positioned within the dialysis cell. The Nelson dialysis cell takes advantage of the fact that it has been known that molecules of various molecular weights can be separated across a semi-permeable membrane. The membrane, by virtue of its composition and consequently its porosity, allows molecules of less than a particular molecular weight to pass through the membrane. Larger molecules are unable to pass through the membrane.

Unfortunately, the Nelson dialysis cell has a complicated construction and is difficult to use. Moreover, after introduction of the buffer into the interior chamber, the dialysis cell must be manipulated in which the inner cylinder must be introduced into the cell. It would be advantageous if the dialysis cell did not need to be manually manipulated in such a manner.

Thus, there is a need for an improved dialysis cell which is easy to use.

It would also be desirable to provide a dialysis cell which was inexpensive to manufacture.

Furthermore, it would be highly advantageous to provide a dialysis cell which can be utilized within a tray storing many cells for use within a laboratory environment.

SUMMARY OF THE INVENTION

Briefly, in accordance with the invention, I provide an improved dialysis cell. The dialysis cell has a polyhedral housing and preferably a hexahedral housing including four sides, a top and a bottom. Preferably, the housing's opposite sides, and top and bottom are substantially parallel. Preferably, the bottom is flat or otherwise constructed so as to be able to rest upon a flat surface without toppling over.

The dialysis cell housing is further constructed in at least two parts including a serum portion and a buffer portion which may be constructed of any number of materials. However, preferred materials for the serum portion and buffer portion include clear non-bioreactive plastics such as acrylic or a crystal styrene which will allow a laboratory technician to visually determine whether a buffer or serum has been introduced into the dialysis cell's interior.

Preferably, the serum portion is also substantially hexahedrally shaped. Furthermore, the serum portion includes a serum cavity for holding a serum specimen and a conduit referred to as a serum specimen inlet for the introduction of a serum specimen. The inlet extends from the top of the serum portion which corresponds to the top of the housing to allow for the introduction of a serum specimen from exterior of the housing into the serum cavity.

The buffer portion is also preferably hexahedrally shaped including a top, a bottom and four sides. The buffer portion's interior side includes a recessed buffer cavity formed on its interior side for holding a buffer. The buffer portion also includes a conduit referred to herein as a buffer inlet. The buffer inlet extends from the top of the buffer portion also corresponding to the top of the dialysis housing for the introduction of a buffer from exterior to the housing into the buffer cavity.

When the serum portion and buffer portion are assembled together to form the hexagonal housing, the serum cavity is positioned to engage the buffer cavity so as to form a central chamber. The dialysis cell further includes a dialysis membrane which is positioned vertically within the housing between the serum portion and buffer portion so as to divide the central chamber and thereby divide the serum cavity and buffer cavity into distinct volumes. In a preferred embodiment, the buffer cavity has a volume of about 1.325 mL and the serum cavity has a volume of about 0.20 mL.

The dialysis cell is constructed so that the dialysis membrane has a liquid tight seal between the serum portion and the buffer portion. In a preferred embodiment, the dialysis cell includes first and second O-rings. A first O-ring is positioned between the serum portion and the dialysis membrane to provide a liquid tight seal, and a second O-ring is positioned between the buffer portion and dialysis membrane to provide a liquid tight seal. The O-rings are positioned concentrically and adjacent to one another to provide the dialysis membrane with a circular region through which molecules of a selected molecular weight are allowed to pass between the serum portion and buffer portion of the dialysis cell.

A customized tray is provided for holding a plurality of dialysis cells. The tray includes a plurality of recesses in which each recess is sized for holding a dialysis cell. The tray may include any number of recesses. However, in a preferred embodiment the tray includes 50 recesses including 5 columns and 10 rows of recesses for neatly arranging dialysis cells for use by a laboratory technician.

Thus, it is an object of the present invention to provide an improved dialysis cell and tray for holding a plurality of dialysis cells.

It is an object of the present invention to provide a dialysis cell which is inexpensive to manufacture and easy to use by lab technicians.

These and other further objects and advantages of the invention will be apparent to those skilled in the art from the following detailed description taken in conjunction with the drawings.

DETAILED DESCRIPTION OF THE INVENTION

Figure 1:
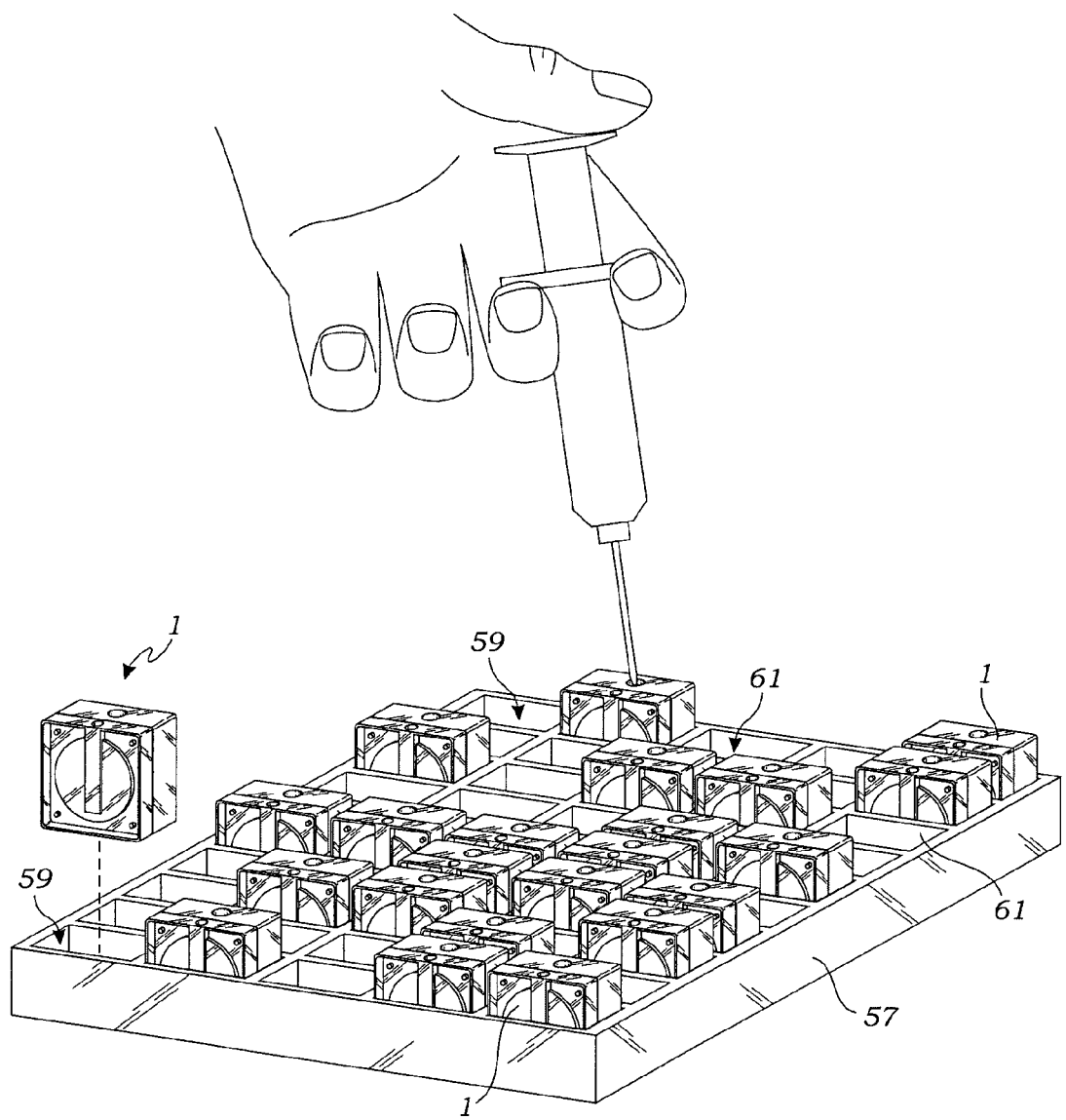
FIG. 1 is a perspective view of a tray and plurality of dialysis cells of the present invention.

While the present invention is susceptible of embodiment in various forms, as shown in the drawings, hereinafter will be described the presently preferred embodiments of the invention with the understanding that the present disclosure is to be considered as an exemplification of the invention, and is not intended to limit the invention to specific embodiments illustrated.

With reference to FIGS. 1-5, the dialysis cell 1 of the present invention includes a housing having a buffer portion 15 and serum portion 29. When the buffer portion and serum portion are assembled together, the dialysis cell preferably has a polyhedral construction. As shown in the drawings, a preferred dialysis cell 1 includes a top 3, a bottom 5, and four sides 7 so as to form a hexahedral construction. Preferably, the top and bottom are flat. Also preferably, the opposing sides 7 of the dialysis cell are parallel.

Figure 2:
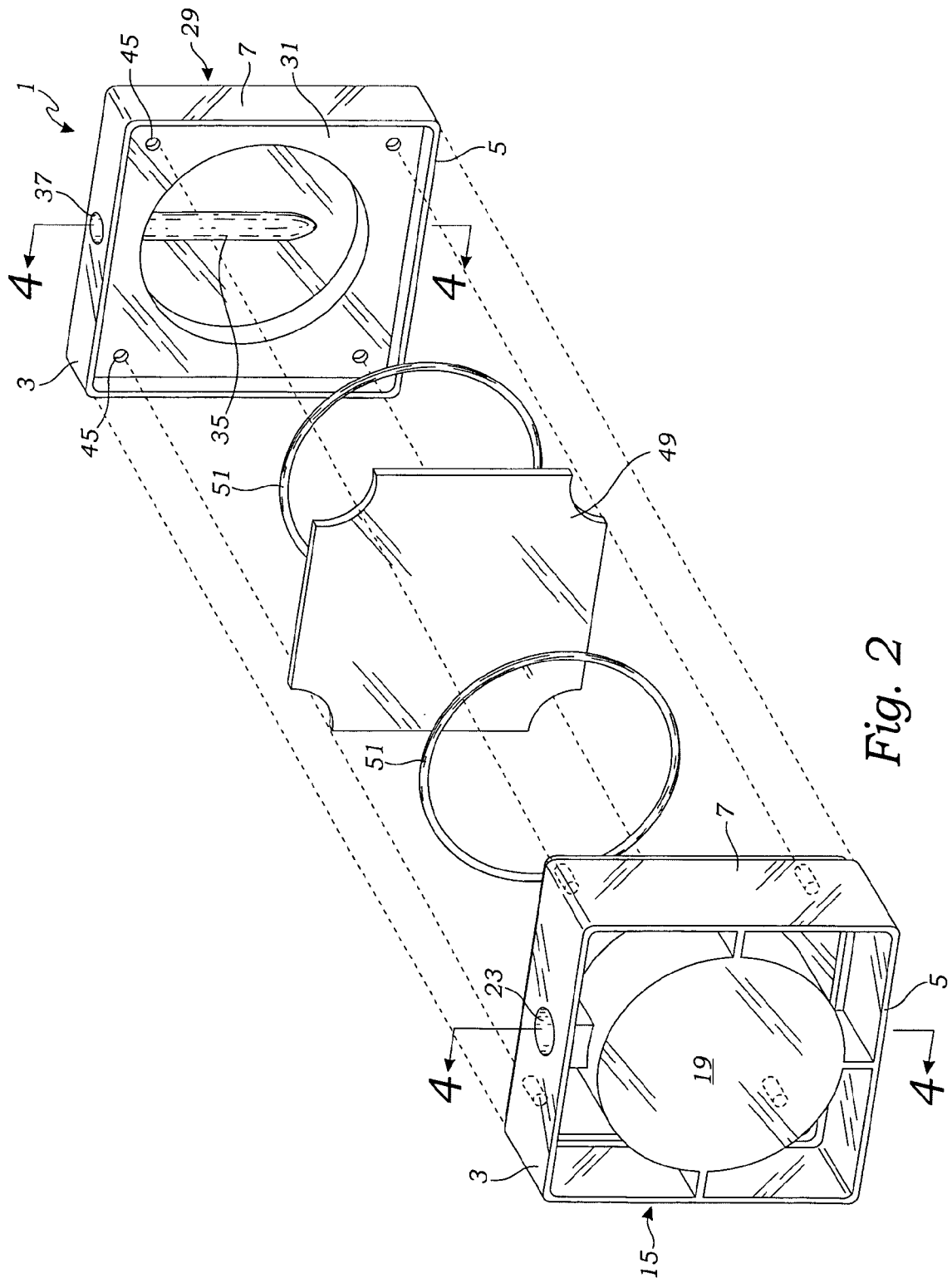
FIG. 2 is an exploded perspective view of the dialysis cell of the present invention.
Figure 3:
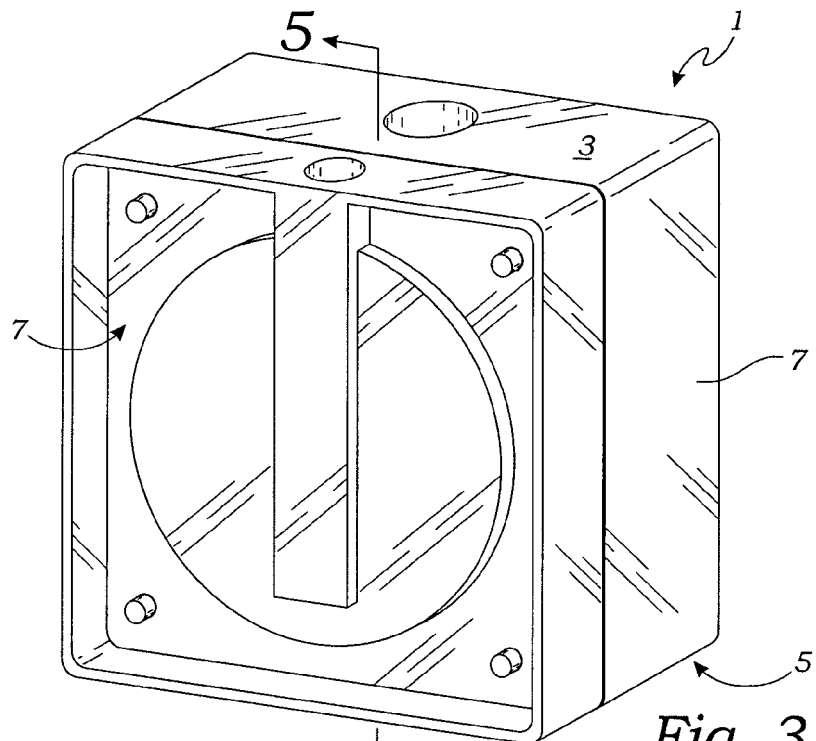
FIG. 3 is a perspective view of the dialysis cell of the present invention.
Figure 4:
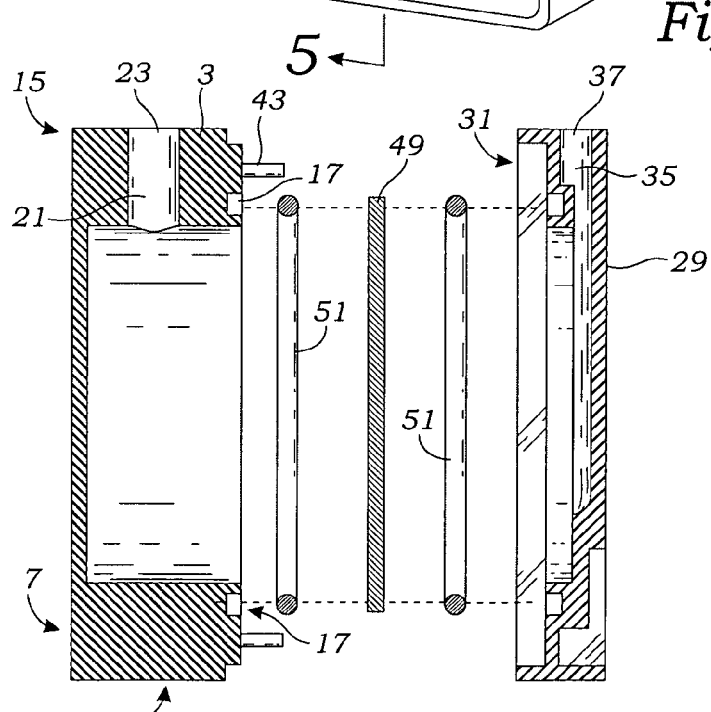
FIG. 4 is a side cutaway view of the exploded dialysis cell shown in FIG. 2.
Figure 5:
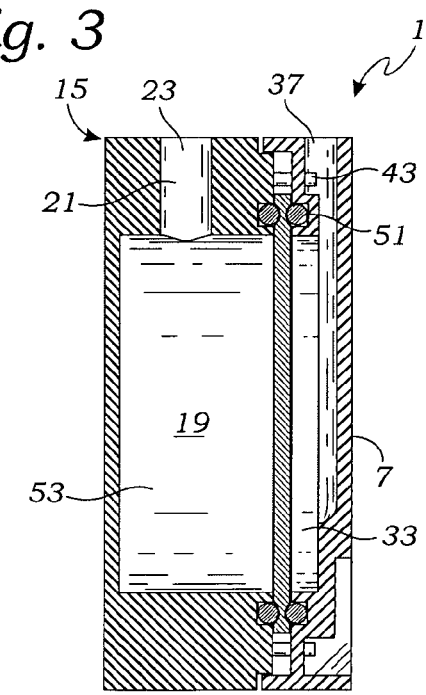
FIG. 5 is a side cutaway view of the dialysis cell shown in FIG. 3.

As best shown in FIGS. 2 and 4, the dialysis cell's buffer portion 15 is preferably hexahedrally shaped so as to include a top 3, a bottom 5, exterior sides 7 and an interior side 17. The interior side 17 includes a buffer cavity 19. Furthermore, the buffer portion includes a buffer inlet 21 and a buffer opening 23 for introduction of a buffer through the opening and inlet into the buffer cavity. The buffer inlet 21 extends from the opening 23 formed on the top surface of the buffer portion 15 to allow for the introduction of a buffer from exterior of the dialysis cell into the buffer cavity 19.

Though perhaps of a smaller size than the buffer portion, the serum portion 29 has a similar construction. To this end, the serum portion 29 is preferably hexahedrally constructed to include a top 3, a bottom 5, exterior sides 7 and an interior side 31. The serum portion also includes a serum cavity 33 which projects inwardly from the serum portion's interior side 31. The serum portion includes a serum inlet 35 which extends from a serum opening 37 formed on the serum portion's top surface to the serum portion's interior cavity 33. The serum portion opening 37 and downwardly projecting serum inlet 35 allow for the introduction of a serum specimen from exterior of the housing into the serum cavity.

When the serum portion 29 and buffer portion 15 are assembled together to form the dialysis cell's housing, the serum cavity is positioned to engage the buffer cavity to form a single central chamber 53. The buffer portion and serum portion may be affixed together using various constructions known to those skilled in the art. As illustrated in the figures, a preferred construction includes providing the buffer portion with four laterally extending prongs 43 sized to reside in a press-fit arrangement within holes 45 formed on the interior side 31 of the serum portion 29. The buffer cavity and serum cavity may be constructed of various sizes. In a preferred embodiment, the buffer cavity is substantially larger than the serum cavity so as to store substantially more buffer than serum. In the preferred embodiment, the buffer cavity has a volume of about 1.325 mL and the serum cavity has a volume of about 0.20 mL. Preferably, the serum opening 37 is also of a different size, and preferably is smaller than the buffer opening. The difference in size is provided so as to clearly delineate which opening is for the introduction of a buffer or serum specimen, respectively. In a preferred embodiment, the serum opening is circular and has a diameter of approximately 0.125 inch and the buffer opening is circular and has a diameter of about 0.185 inch.

The dialysis cell 1 further includes a dialysis membrane 49 which may be made of various materials. However, a preferred dialysis membrane is made of regenerated cellulose having a molecular weight porosity of 12,000 to 14,000 which is supplied by Spectrum Laboratories. The membrane 49 is positioned to extend vertically and be sandwiched between the serum portion 29 and buffer portion 15 so as to divide the central chamber 53 into the separate serum cavity 33 and buffer cavity 19.

The dialysis membrane 49 includes a central region wherein molecules smaller than a predetermined size can travel from the buffer cavity to the serum cavity and vice versa so as to allow liquids within the central chamber 53 to reach equilibrium. However, the membrane is sealed around its periphery so as to provide a liquid tight seal with both the serum portion and buffer portion. In a preferred embodiment illustrated in FIGS. 4 and 5, the dialysis cell 1 includes a pair of O-rings 51 in which a first O-ring compresses between the buffer portion and dialysis membrane and a second O-ring compresses between the dialysis membrane and serum portion. The O-rings are preferably made of medical grade silicone, and are positioned vertically and adjacent to one another to provide the dialysis membrane with a circular region through which molecules of a preselected molecular weight are allowed to pass.

In a preferred embodiment illustrated in FIG. 1, a tray 57 is provided for storing a plurality of dialysis cells. The tray 57 includes several recesses 59 in which each recess is sized to hold one dialysis cell. Each recess includes a bottom and a plurality of sides 61 which are sized and positioned so as to allow receipt of a dialysis cell. As illustrated in the figures, preferably each recess 59 includes four sides sized for receipt of the hexahedrally shaped dialysis cells shown in FIGS. 2-5. The tray may include any number of recesses. However, in the preferred embodiment illustrated in FIG. 1, the tray includes fifty recesses comprising five columns and ten rows. Preferably, the recesses are spaced apart sufficiently so as to facilitate insertion and withdrawal of dialysis cells by laboratory technicians.

In operation, one or more dialysis cells are introduced into the recesses of a tray 57. With reference to a single dialysis cell, buffer is introduced into the cavity formed within the buffer portion of the dialysis cell, and serum is introduced into the cavity formed in the serum portion of the dialysis cell. As understood by those skilled in the art, various buffers may be employed. However, preferred buffers are available from IVD Technologies, Inc. of Santa Ana, Calif. As illustrated in FIG. 1, introduction of the buffer and/or specimen may be introduced into their respective interior cavities by use of a syringe or the like projecting through the openings and inlets formed within the buffer portion and serum portion. Pipettes or similar constructions may also be used. The dialysis cell is then left to allow the liquid within the central chamber 53 to reach equilibrium. Thereafter, a sample is withdrawn from the dialysis cell's central chamber, preferably by introduction of a syringe needle through the buffer inlet 21. The needle's plunger is drawn back so that a sample is drawn into the syringe barrel. Thereafter, the sample is analyzed to measure for free thyroxine ($T_4$).

While several particular forms of the invention have been illustrated and described, it will be apparent that various modifications can be made without departing from the spirit and scope of the invention. Therefore, it is not intended that the invention be limited except by the following claims.

Having described my invention in such terms so as to enable persons skilled in the art to understand the invention, recreate the invention and practice it, and having identified the presently preferred embodiments thereof, I claim:

1. A tray and dialysis cell combination comprising:
    a horizontally extending tray having a top and a bottom, said top having a plurality of recesses having a bottom and a plurality of sides;
    a plurality of dialysis cells positioned within but manually removeable from at least some of said recesses, each of said dialysis cells including:
    a. a housing including a top and divided into a serum portion and a buffer portion;
    b. said serum portion including a serum cavity for holding a serum specimen, said serum cavity being substantially cylindrical having a substantially horizontal central axis, said serum portion further including a serum specimen inlet for introduction of a serum specimen from exterior to said housing into said serum cavity, serum inlet extending from an opening formed on said housing top to said serum cavity for the gravity introduction of a serum through said serum inlet into said serum cavity;
    c. said buffer portion including a buffer cavity for holding a buffer, said buffer cavity being substantially cylindrical having a substantially horizontal central axis, said buffer portion further including a buffer inlet for introduction of a buffer from exterior to said housing into said buffer cavity, said buffer inlet extending from an opening formed on said housing top to said buffer cavity for the gravity introduction of a buffer through said buffer inlet into said buffer cavity;
    d. said serum cavity positioned adjacent to said buffer cavity with the serum portion's center axis coincident with buffer cavity's center axis so that said serum cavity and said buffer cavity form a single substantially cylindrical central chamber within said housing also having a substantially horizontal central axis; and
    e. a dialysis membrane sandwiched between said serum portion and said buffer portion having a porosity allowing for the passage of molecules smaller than a predetermined molecular weight, said dialysis membrane vertically positioned between serum portion and said buffer portion to separate said chamber into said serum cavity and said buffer cavity,
    said dialysis cells constructed so that when said buffer inlet and said serum inlet are positioned at the top of said dialysis cells for the gravity introduction of a serum through said serum inlet into said serum cavity and for the gravity introduction of a buffer through said buffer inlet into said buffer cavity, said cylindrical central chamber's central axis being substantially horizontal and said dialysis membrane being positioned substantially vertically and perpendicular to said cylindrical central chamber's central axis.

2. The tray and dialysis cell combination of claim 1 further comprising:
    a first O-ring positioned to provide a liquid tight seal between said serum portion and said dialysis membrane; and
    a second O-ring positioned to provide a liquid tight seal between said buffer portion and said dialysis membrane.

3. The tray and dialysis cell combination of claim 1 wherein said buffer cavity has a volume of about 1.325 milliliters and said serum cavity has a volume of about 0.20 milliliters.

4. The tray and dialysis cell combination of claim 1 wherein said buffer portion opening for introduction of a buffer is substantially larger that said serum portion opening for introduction of a serum.

5. The tray and dialysis cell combination of claim 4 wherein said buffer portion opening for introduction of a buffer is circular and has a diameter of about 0.185 inch and said serum portion opening for introduction of a serum is circular and has a diameter of about 0.125 inch.

\* \* \* \* \*